United States Patent [19]
Spink et al.

[11] Patent Number: 5,841,149
[45] Date of Patent: Nov. 24, 1998

[54] METHOD OF DETERMINING THE DISTANCE OF A FEATURE ON AN OBJECT FROM A MICROSCOPE, AND A DEVICE FOR CARRYING OUT THE METHOD

[75] Inventors: Roger Spink, Balgach; Bernhard Braunecker, Rebsteom, both of Switzerland; Klaus-Peter Zimmer, Heerbrigg, Switzerland; Thomas Mayer, Hohenems, Austria; John Rice Rogers, Heerbrugg, Switzerland

[73] Assignee: Leica Mikroskopie Systeme AG, Heerbrugg, Switzerland

[21] Appl. No.: 722,021
[22] PCT Filed: Apr. 9, 1995
[86] PCT No.: PCT/EP95/01301
  § 371 Date: Dec. 12, 1996
  § 102(e) Date: Dec. 12, 1996
[87] PCT Pub. No.: WO95/27917
  PCT Pub. Date: Oct. 19, 1995

[30] Foreign Application Priority Data

Apr. 11, 1994 [CH] Switzerland .............................. 1088/94
Apr. 11, 1994 [CH] Switzerland .............................. 1089/94
Apr. 11, 1994 [CH] Switzerland .............................. 1090/94
Apr. 11, 1994 [CH] Switzerland .............................. 1091/94
Apr. 11, 1994 [CH] Switzerland .............................. 1092/94

[51] Int. Cl.$^6$ ............................ G01N 21/86; G01B 11/24
[52] U.S. Cl. .................................. 250/559.29; 250/201.3; 356/359; 356/376
[58] Field of Search ........................... 250/201.3, 559.29; 356/375, 376, 345, 359

[56] References Cited

U.S. PATENT DOCUMENTS

| | | | |
|---|---|---|---|
| 4,576,479 | 3/1986 | Downs | 356/359 |
| 5,042,949 | 8/1991 | Greenberg et al. | 356/359 |
| 5,359,417 | 10/1994 | Müller et al. | 250/201.3 |
| 5,513,005 | 4/1996 | Müller et al. | 356/375 |

FOREIGN PATENT DOCUMENTS

| | | |
|---|---|---|
| A-0094835 | 11/1983 | European Pat. Off. . |
| 41 34 481 | 4/1993 | Germany . |
| WO-A-9011487 | 10/1990 | WIPO . |
| 95/27226 | 10/1995 | WIPO . |
| 95/27918 | 10/1995 | WIPO . |

*Primary Examiner*—Stephon B. Allen
*Attorney, Agent, or Firm*—Foley & Lardner

[57] ABSTRACT

The invention is directed to a surgical microscope in which, to determine the distance between the microscope (8, 13) and the object (22), the travel time of a beam of light (57c) emanating from the microscope and reflected by the object is determined. The travel time is determined by phase measurement or by interference matching. In the case of direct phase measurement, modulated light is used. In the case of interference matching, partly coherent light is used. In order to ensure high accuracy over wide measurement range, the two measurement methods are preferably used in combination.

17 Claims, 6 Drawing Sheets

METHOD OF DETERMINING THE DISTANCE OF A FEATURE ON AN OBJECT FROM A MICROSCOPE, AND A DEVICE FOR CARRYING OUT THE METHOD

BACKGROUND

The invention relates to a method according to claim 1 and a device according to claim 10.

For an operating surgeon, surgical microscopes serve the purpose of optical magnification of the site in which an operation is to be carried out. There are basically three different types of surgical microscopes, which are all intended within the meaning of the invention. These are,:

1. purely optical microscopes, that is to say microscopes which contain only optical and mechanical components, their output being directed to the eye;

2. purely video microscopes, that is to say microscopes which have optical, mechanical and optoelectronic components, the optical output of the microscope being directed exclusively to an optoelectronic image pick-up device (for example, a CCD), and the recorded image being further processed exclusively electronically and possibly represented via a display; and, 3. mixed video microscopes, which jointly contain structural features of the microscopes according to the first-named and second-named points, that is to say an output is directed both directly to a visual observer and to an image pick-up device.

In order to achieve on every occasion an optimum representation of the operation site, it must be possible always to position the visual field plane on a feature on the object to be treated. Since, because of the object structures represented, it is frequently impossible to achieve the focusing, it is necessary to provide a method and a device which render it possible to superimpose the visual field plane and the feature on the object and to determine the position of a feature on the object. Precise knowledge of the position of the feature of the object is important chiefly wherever specific, previously determined depths of incision or lengths of incision are to be observed, or wherever the operating surgeon has to keep an operating instrument to specific wavelengths in order to be able to carry out a precise operation. Chiefly in the case of operations on the brain and in microsurgery, this is frequently imperative in order to avoid injury to healthy tissue. In such operations, the result of the operation (whether a complete success or death) frequently depends on fractions of millimeters. Consequently, efforts have been made to determine the sites as accurately as possible and to permit dimensional measurements. Reference may be made to German Patent Application DE-A-4134481 for an example of such a known design.

In the abovementioned German Application, a surgical microscope is described in which the aim is to perform a precise determination of the location on an object being viewed of a specific point generated by means of a laser beam. Proposed for this purpose is a sighting method in which exact focusing of the microscope or matching of the visual field plane and the feature of the object is achieved by the "bringing into coincidence" of visual field marks. Not until after this sighting method is the exact position of the marked feature on the object determined from the optical system data. In accordance with the this technique, these system data are intended to be determined by suitable position detectors or angle detectors on drive units for the respective adjustment of adjustable optical components.

The determination of the position of a feature on an object is thus performed indirectly after the "bringing into coincidence" by eye, or via an image-processing device by measuring paths, angles etc. via sensors which are connected to adjusting devices for optical components and via subsequent calculation of the corresponding data.

This is unsatisfactory and insufficient in many cases. Even the "bringing into coincidence" is affected by errors. A further reason for inaccuracies resides in the fact that both the optomechanical components and the mechanical/electrical components (sensors) have tolerances which can vary nonlinearly. The result of this is the risk that position data determined in such a way are incorrect. In the extreme case, such incorrect data could lead to serious errors in the work of the operating surgeon. Calibration measurements on the patient—which are provided imperatively in accordance with the this technique—can somewhat lessen such errors. However, it is precisely these calibration measurements which are not undisputed and which are, above all, dependent on the human performance of the operator. The known attempt to detect mechanical tolerances of the magnifying system when assembling the microscope and to determine therefrom a correction curve which is superimposed on the current data is unsatisfactory to the extent that tolerances can change as a function of innumerable factors and the correction curves then used are of no assistance. Furthermore, determining such correction curves itself is problematic, and above all time-consuming. In addition, an appropriate correction program requires additional computer power and may reduce the computer speed in the real time area.

If the preferred laser triangulation principle is used in the sighting method, it is necessary to select a beam path which in the case of the object provides an angle between the incident beam and the reflected one. This angle causes problems in the case of features on an object which are located in depressions, since the lateral edges of the depressions may interrupt a beam path obliquely outward.

SUMMARY OF THE INVENTION

It is therefore on the object of the invention to develop a method in which the abovementioned disadvantages are avoided and it is possible to determine positional data quickly and reliably even for objects having an uneven surface.

In achieving this object, in a first inventive step it is detected that the position of a feature on an object is measured directly and not by means of a sighting method and the subsequent determination of positional data of the optical system. The object position can be determined directly in this case, without the need to perform focusing onto a feature on the object. If necessary, the visual field plane can be brought into coincidence with the specific position of the feature on the object by adjusting the optical system. In a second inventive step, it is detected that for the purpose of directly determining the position of a feature on the object, the path length along a light bundle is determined between a reference plane and the feature on the object. More precisely, this length is the distance between the intersections of the microscope's center axis (or optical axis) with the reference plane and with the detail of the object. Three related methods are to be understood as the determination of this path length within the meaning of the invention: measurement of the transit time of a light pulse, phase measurement on a modulated light beam, the modulation possibly affecting either the intensity or the polarization of the beam, and measurement of the coherence relationship between a reference beam and a measuring beam.

These methods have in common that the length of the path from the reference plane to the feature on the object is measured with the aid of the known rate of propagation of a light pulse.

Phase measurement within the meaning of the invention is to be understood as determining the phase difference between the modulation functions of emitted and received light signals, for example light pulses, the modulation being impressed on the light bundle by means of temporal variation, for example of the intensity of the light source. This measuring method can be understood in the following way as an extension of the transit-time method, since a temporal sequence of emitted light pulses of variable intensity can be described mathematically as a periodically modulated wave. The time delay caused by the finite speed of the light is revealed in accordance with this as a phase shift in the modulation function of the received signal with respect to that of the emitted signal. Measurement of this phase shift is thus equivalent to a transit-time measurement.

The determination of the transit time as the phase difference of two signal functions can also be implemented in a purely optical fashion.

For this purpose, the light wave which traverses the measuring distance to the object there and back, is compared with a suitable reference wave. For this purpose, the two waves must be optically superimposed. However, the superimposition produces a signal—stationary over a certain period—only when the two waves have a fixed mutual phase relationship. This time of the temporal phase constant is termed the coherence time; the path the wave propagates during this time is termed the coherence length. Depending on the mode of generation of the light, this length can be between fractions of a mm up to 10 kilometers. In practice, the procedure is that the emitted wave is resolved into two components, of which one traverses the actual measuring distance while the other traverses a suitable reference distance. If both distances are now tuned in such a way that their difference is within the coherence length of the light, the optical superimposition of the two waves on a detector produces a more or less contrasting, interferometric pattern which is easy to measure or detect electronically. The contrast is known to be greatest when the optical paths or, which is the same thing, the transit times of the light are identical in both arms of the interferometer. The value of the distance to the feature on the object which is to be determined is inferred from the determination of the current length of the reference distance. This distance measurement in the reference arm can be done mechanically or by means of one of the other methods.

Use is made of a temporally modulated light source (which is, for example, a light-using diode—LED—driven in a pulsed fashion or an LED upstream of which a shutter driven in a pulsed fashion—for example, an LCD—is connected) for measuring the transit time or phase while, as stated, partially coherent light is used to measure the interference. In physical terms, partially coherent light within the meaning of the invention is to be understood as light which has a finite spectral bandwidth, that is to say different "colors". In this case, however, their frequencies are still so similar that the emitted light has phase-locked, that is to say coherent properties in a limited range, the coherence length being smaller than, for example, in the case of highly coherent lasers. Typical coherence lengths which are reasonable in accordance with the invention extend between 1 mm and 1 m—depending on the distances to be expected between the microscope and the feature on the object.

A modulated light source is, preferably, a modulated semiconductor laser, possibly a modulated LED whose light intensity is preferably modulated sinusoidally, but possibly in a triangular fashion. The modulation frequency is at least 10 megahertz, and preferably between 30 and 200 megahertz, in particular approximately 100 megahertz. The corresponding modulation wavelengths are preferably between 10 m and 1.5 m, in particular approximately 3 m. Since the light path corresponds to twice the measuring distance, the measurable measuring distances are less than half the modulation wavelengths. The measuring accuracy depends on the determination of the phase of the modulation function and is to be in the range of a few millimeters, but preferably of fractions of a millimeter.

The measuring accuracy which is achieved in the case of interference matching using partially coherent infrared light with wavelengths of approximately 100 $\mu$m to 0.7 $\mu$m, or with visible light with wavelengths of 0.7 $\mu$m to 0.4 $\mu$m is a few micrometers or fractions of a micrometer. Since at these high accuracies small measuring distances are concerned, it is expedient to use a coarse adjustment or coarse measuring device in addition to the interference matching.

An advantageous embodiment provides that the above-described determination of position by means of modulated light is used as coarse measuring device, with the result that it is possible together with interference matching to determine the position of the object in a wide measuring range with extremely high accuracy. In addition to this high accuracy and range, the described method has a further important advantage over the known triangulation methods. Specifically—to the extent that the measuring beam is only narrow enough—a surface structure of the object which causes strong scattering of the reflected bundle does not lead to a worsening of the measuring accuracy in the case of distance measurement. By contrast, in the triangulation method the accuracy of the sighting method, in particular of the "bringing into coincidence" is impaired by strongly scattering and poorly reflected bundles.

It is important in this case in most applications that the measuring light bundle is guided onto the feature on the object in the immediate vicinity of the central axis of the microscope, and that it is directed—before it impinges on the feature on the object—with its central axis of the bundle as parallel as possible, that is to say at no angle, or at most at a small angle, to the central axis of the microscope. This measure according to the invention renders it possible to determine the position of the microscope relative to the features on the object even through relatively narrow cavities. It is therefore also reasonable to scan the measuring light bundle in a region concentric with the central axis, just mentioned, of the light bundle, as soon as it is reflected or scattered by the feature on the object.

The distance measurement according to the invention provides a light path having a first subpath from the optical system to the object and a second subpath from the object back to the optical system, with the result that in essence a vanishingly small angle is arranged between the two parts of the light path. In particular, the two subpaths are arranged coaxially and essentially parallel to, but also preferably coaxially with the optical axis. This arrangement is possible because of the renunciation of triangulation, and has the advantage that measurements can be undertaken without any problems even in depressions.

The light can be launched at the start of the first subpath by the electronic measuring system via light guides and an inserting element, and extracted similarly at the end of the second subpath via extracting elements and light guides and fed to the electronic measuring system. The light path can also possibly start and/or end to the side of the optical system. It is thus possible to select a simple design which scarcely impairs the optical properties of the microscope. Because of the slimness of a measuring light bundle, which is preferably obtained from a laser beam, an inserting or extracting element can have very small dimensions. Moreover, it can be arranged in the immediate vicinity of the main objective, with the result that it is below the limit of detectability optically, since it is near the pupil. All reflecting components, such as beam splitters, mirrors, reflecting prism faces etc. basically come into consideration as inserting and extracting element elements.

One of the two abovementioned solutions, also to be applied independently, of another object arises from the application of a flat glass sheet as a backing plate for the inserting elements. Such a backing plate permits the dimensions of the relevant optical components to be minimized and the components to be brought up close to the main objective. In this case, the assembly and the mechanical structure of such components and of their mounting device are also particularly simple.

In accordance with a special embodiment of the invention, the portion of the measuring light bundle passing through the beam splitter for extraction is filtered out by a narrow-band filter, or the measuring light is selected from a spectral region to which the human eye is insensitive.

The invention can also be applied in all types of microscopes other than those mentioned above, it also being possible in the case of video microscopes for the pixel produced on the image pick-up device (for example, on the CCD) to be removed electronically, in particular whenever it can be detected on the receiving CCD because of a special temporal modulation.

The invention is described in particular in connection with a surgical microscope. However, in the widest sense, it can also be applied expediently with any other microscopes and also in the case of endoscopes.

With regard to the method for determining positional data, reference is made, in particular, to the descriptive parts of the abovementioned German Application, which are deemed to be disclosed within the framework of this description. These are, in particular: column 2, line 13 to column 4, line 5 as well as FIGS. 2–4 and the associated descriptive parts. With regard to the possibility of superimposing image data, reference is also made to the PCT Patent Application WO-A-95 27 226 and WO-A-95 27 918, whose corresponding descriptive parts and figures are deemed as being disclosed within the framework of this application.

Also within the framework of the invention are various other methods, types of embodiments and variants which are characterized or described.

BRIEF DESCRIPTION OF THE DRAWINGS

Further details and embodiments of the invention follow from the drawings, in which.

DETAILED DESCRIPTION OF THE PREFERRED EMBODIMENTS

The figures will be described coherently. Identical reference symbols denote identical components. Identical reference symbols with different indices denote similar components, or ones of similar function. The invention is not restricted to the exemplary embodiments represented.

Figure 1:
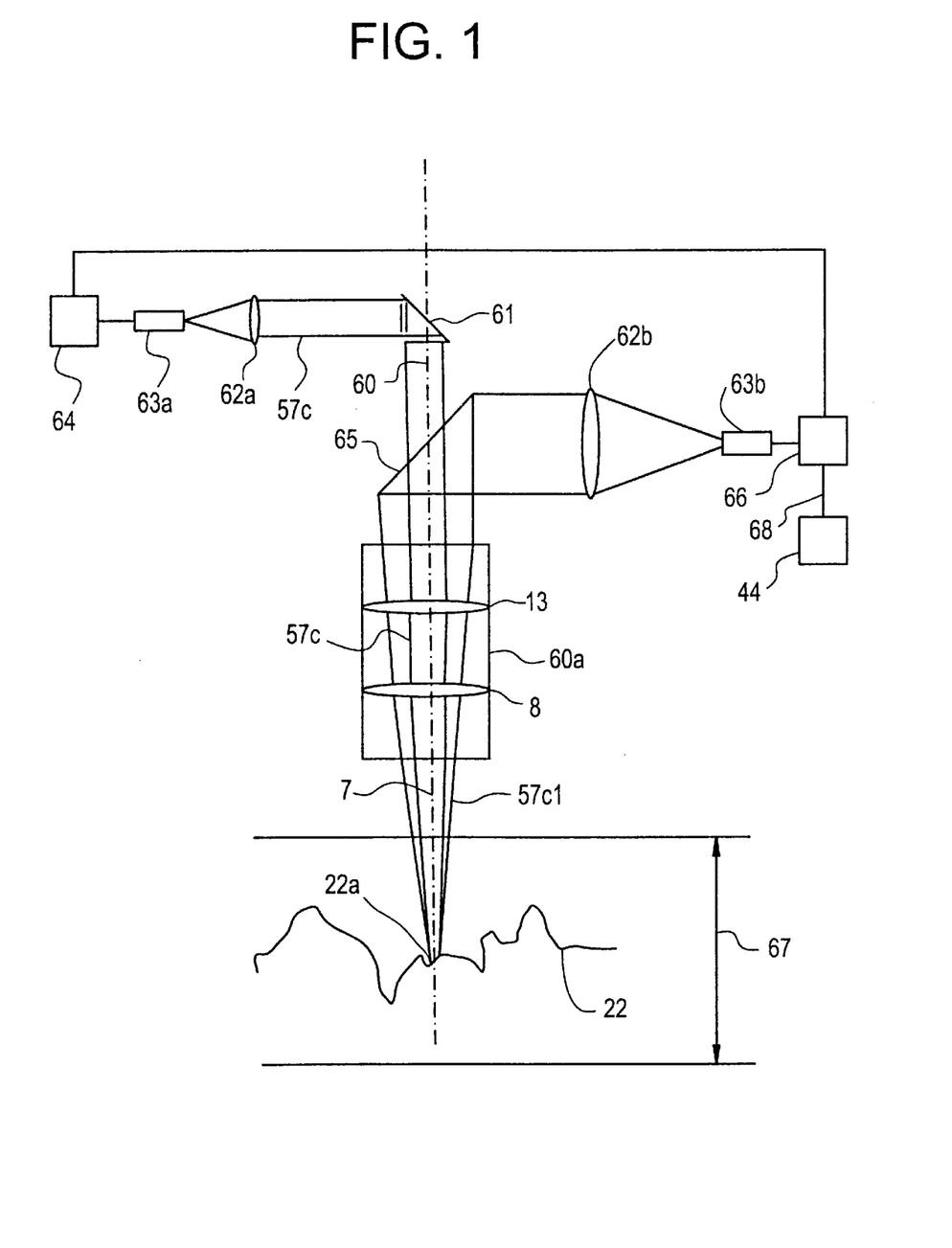
FIG. 1 shows a diagrammatic representation of a setup for measuring the distance between the microscope and the object.

FIG. 1 shows a microscope beam path 60*a* with a schematically indicated main objective 8 and a zoom lens 13. Arranged downstream of the zoom lens 13, essentially in the region of the optical axis 7 of the beam path 60, is a deflecting element 61 as an inserting element for a light bundle 57*c*, which is incident transverse to the optical axis 7. The holder of the deflecting element 61 is not represented, since a number of holders are known to every person skilled in the art. The incident light bundle is generated in a light source 64 and preferably guided through a light guide 63*a* and a focusing element 62*a* toward the deflecting element 61. From the deflecting element 61, the light bundle 57*c* passes, preferably along the optical axis 7, to the object 22, where it is reflected at a feature 22*a* on the object and passes through the microscope optical system 8, 13 to a second deflecting element 65 and is fed there transverse to the optical axis 7 to a sensor 66, possibly through a focusing element 62*b* and a light guide 63*b*. The light source 64 and the sensor 66 are preferably connected to one another, in particular it is a measuring system having a light guide output 63*a* and a light guide input 63*b*.

The light source 64 supplies a modulated light having a preferably sinusoidal, but possibly triangular, periodic fluctuation in intensity. It is preferable to use a modulated laser, but possibly also a modulated LED. A direct determination of the phase shift of the modulation signal on the light path from the light source 64 to the sensor 66 is determined in the sensor 66 or in the measuring system 64, 66. This phase shift is rendered accessible via a line 68 to a microprocessor 44. The processor 44 determines the distance between the microscope and object from the phase shift of the modulation function, the modulation frequency or the modulation wavelength and the system dimensions. The processor 44 can be used to adjust the microscope optical system in such a way that the visual field plane comes to lie at the specified distance.

The measuring range for the entire light path is essentially a modulation wavelength. In the case of modulation frequencies of 50 or 200 MHz, the result is well-defined measuring ranges of, for example, 6 m and 1.5 m, respectively. The effectively required distance range 67 in which the object can be moved and in which the distance must be measurable is very small in the case of a microscope. In the case of the frequencies specified above, the distance range 67 corresponds only to a small portion of half the measuring range, with the result that the distance can be uniquely determined.

In order to achieve as high an accuracy as possible, the modulation frequency should be chosen as high as possible. Currently known lasers cannot be modulated with frequencies up to approximately 100 MHz. However, it has already proved possible to achieve measuring accuracies in the range of millimeters and fractions thereof with the aid of a commercially available, phase-determining "Distomat" distance measuring device from Leica AG, which is used in the sphere of measurement.

If the bundle 57c1 reflected at the object 22 diverges strongly, a portion of the measuring beam 57c1 can pass to the viewers eye laterally next to the second deflecting element 65. In order to prevent unnecessary loading of the observer's eye and/or impairment of the image quality, it may be provided that the measuring beam is emitted only as the case may be, in particular, after changes in position of the microscope and/or after changes in the object surface. An interval switch, which periodically interrupts the light emission of the light source 64, may also be provided. Since disturbances of the beam path of the microscope also proceed from the deflecting elements 61, 65, designs are provided in which the deflecting elements are arranged displaceably and are not moved in the beam path of the microscope until required.

A color filter may be provided for the purpose of reducing the light from the light source 64 which passes to the observer. The filter is preferably very narrowband and filters out precisely only the wavelength region of the measuring beam 57c1 which is situated in the infrared, for example.

Figure 2:
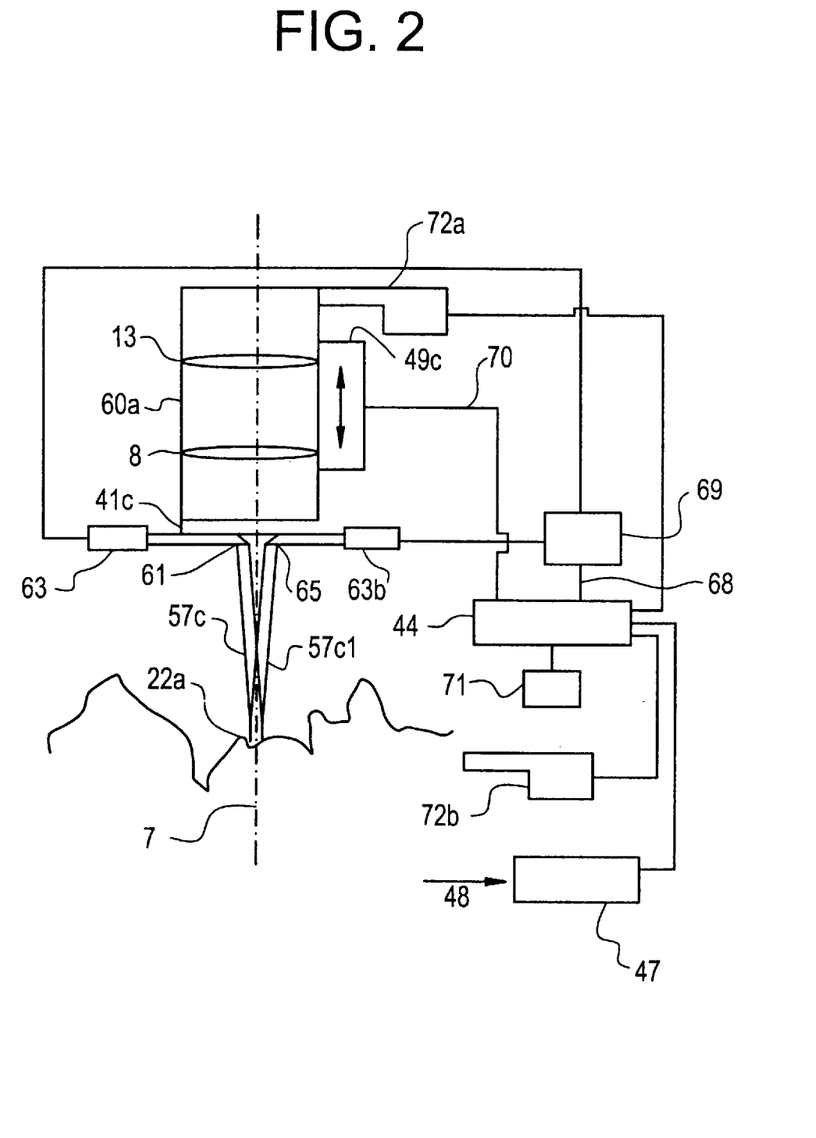
FIG. 2 shows a distance measurement in accordance with FIG. 1, but with the light source and sensor spatially combined.

FIG. 2 shows an embodiment in which, for the purpose of distance measurement, the light source and the light sensor are spatially combined in a distance measuring system 69, starting from which the measuring light is guided via light guides to the inserting or extracting tail 63a and 63b, respectively. Use is made of laser light of which the beam 57c is launched between the object and the microscope by the first deflecting element 61. In this arrangement, the deflecting element 61 is fastened to a backing plate 41c and situated somewhat offset alongside the optical axis 7. The beam 57c1 reflected at the feature 22a on the object is directed by the second deflecting element 65 toward the light guide tail 63b connected to the sensor. The second deflecting element 65 is likewise arranged on the backing plate 41c by analogy with the deflecting element 61.

The measuring system 69 is connected to the microprocessor 44 via at least one line 68. The microprocessor 44 also contains all microscope data from the measuring system 69 in addition to the distance information. Thus, for example, it is possible via a connection 70 for the adjusting device 49c for the microscope optical system to be controlled and for its current setting to be retrieved. After the object distance has been determined, it is thus possible by readjustment to focus the microscope optical system optimally to the distance determined. However, the focusing can also be set to a specific difference above or below the object distance, which is frequently mandatory in medical applications.

Since the object surface observed by the microscope sometimes has structures which are difficult to interpret, it is then expedient to be able to assign information from other imaging methods such as, for example, MRI data or X-ray data, to the observed object in a dimensionally accurate fashion. For this purpose, in addition to the distance between the microscope and object it is also necessary to detect the position and alignment of the microscope and the magnification of the latter and the position of the focal plane. In order to determine magnification data, provision is made for a magnification measuring unit 71 which preferably detects the optical deflection of at least one light beam being guided through the microscope optical system. At least one position determining system 72a, 72b is provided for the purpose of detecting the position and alignment of the microscope and/or of the object.

The processor 44 is connected to the magnification measuring unit 71, the position determining system 72 and, via an image data transmission module 47 to an external image data input 48.

Figure 3:
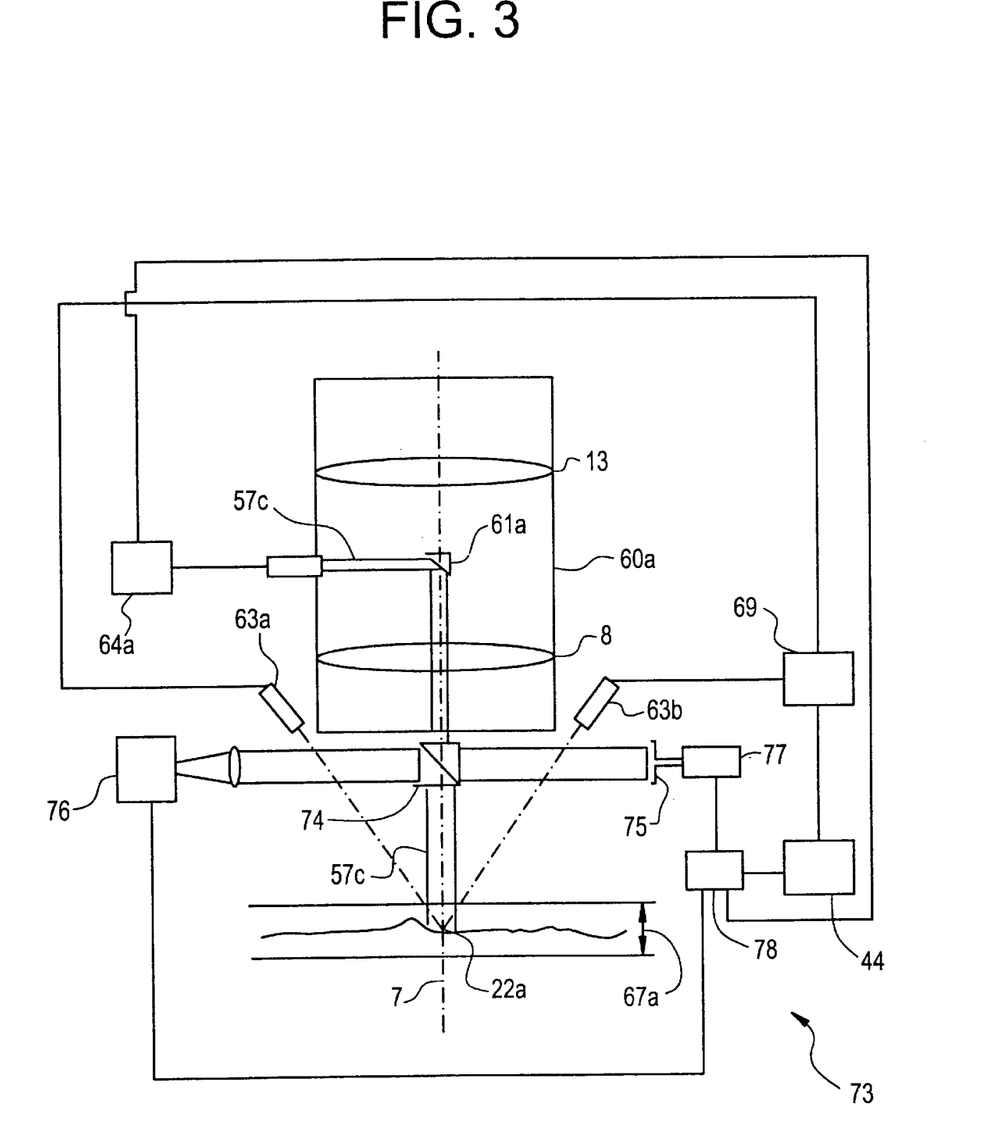
FIG. 3 shows a distance measurement in accordance with FIG. 2, including an interferometric unit for fine resolution.

FIG. 3 shows an embodiment having an interferometer which guides a partially coherent beam 57c to the feature 22a on the object from a light source 64a via a deflecting element 61a, and essentially coaxial with the optical axis, through a semireflective mirror 74. A portion of the beam 57c is deflected transverse to the optical axis by the semi-transmitting beam splitter 74 to an adjustable reflector 75 over a matching path. The component beam reflected at the object and the component beam reflected at the reflector pass through the semitransmitting beam splitter 74, with deflection or straight, to a detector 76. The reflector 75 is adjusted by means of an electromechanical adjusting element 77 until interference patterns are formed in the detector. An interferometer controller 78 is connected to the detector 76, the adjusting element 77 and the laser 64a in order to control and evaluate the interference measurement. The adjustment of the reflector 75 corresponds to length matching and can be used to determine the object position. The distance determined can be fed to the processor 44 by the interferometer controller 78 via a connection.

Since the measuring range 67a of the interferometer is restricted, a coarse measuring device, in particular a distance measuring system 69 with direct phase measurement of a modulated signal, is preferably provided. The light guide tails 63a, 63b are aligned in the embodiment represented at an acute angle to the optical axis 7. The measured values of the measuring system 69 and of the interferometer 73 are combined in the processor 44 to an extremely accurate specification of the distance.

Figure 4:
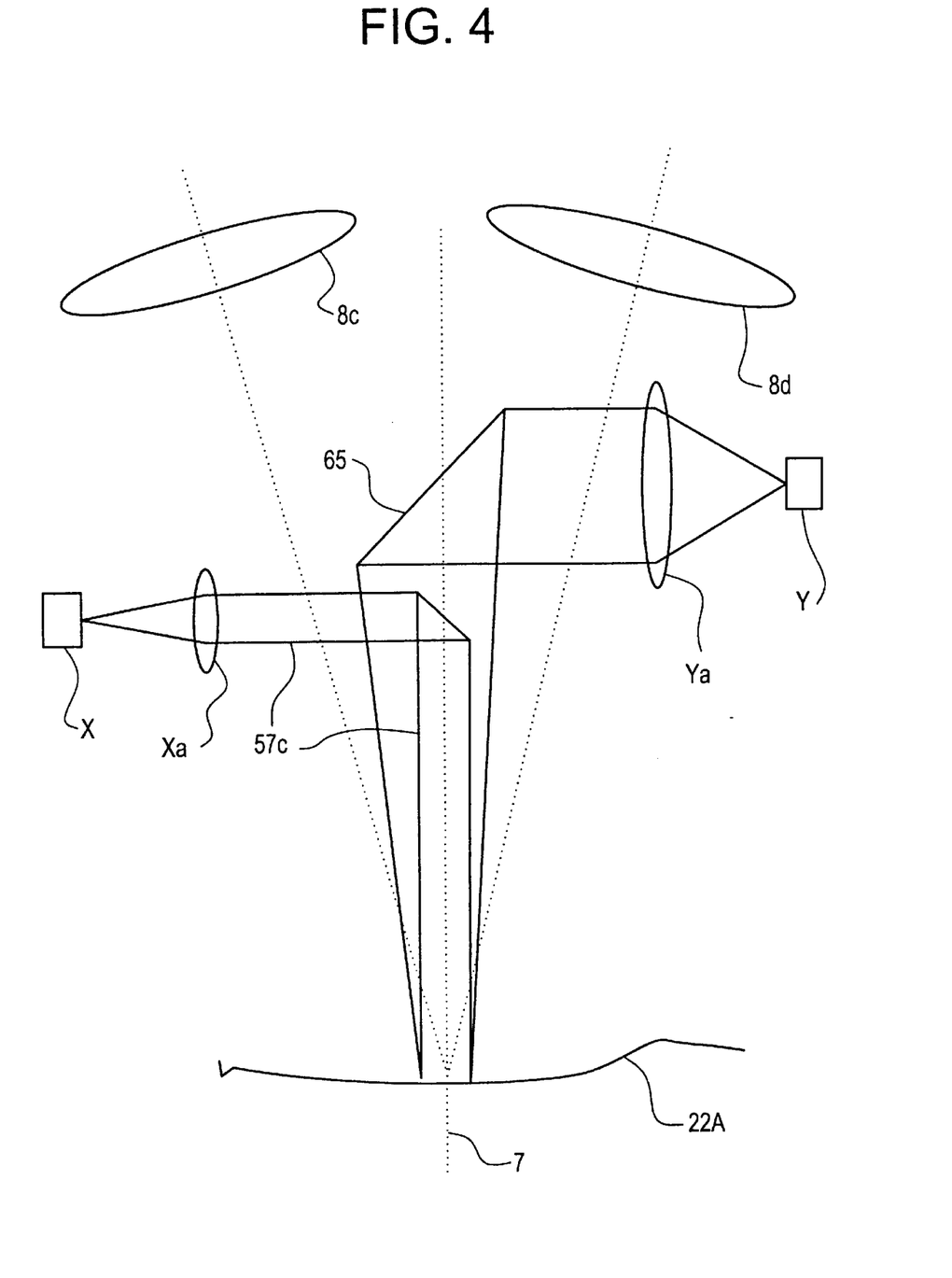
FIG. 4 shows a distance measurement in accordance with FIG. 1 for microscopes having separate main pupils (Greenough type)

FIG. 4 is a diagrammatic representation of the measuring arrangement in conjunction with a microscope arrangement having two main objectives 8c and 8d (Greenough), without a common main objective. Via the optical feeding system Xa, a measuring beam 57c passes from a light source X directly, or via a tail X of an interposed light guide and preferably parallel to and symmetrically with respect to the optical axis 7 to the object 22A. The scattered light is fed via a mirror 65 and an outcoupling optical system Ya to a detector Y directly, or to a tail Y of a further light guide.

Figure 5:
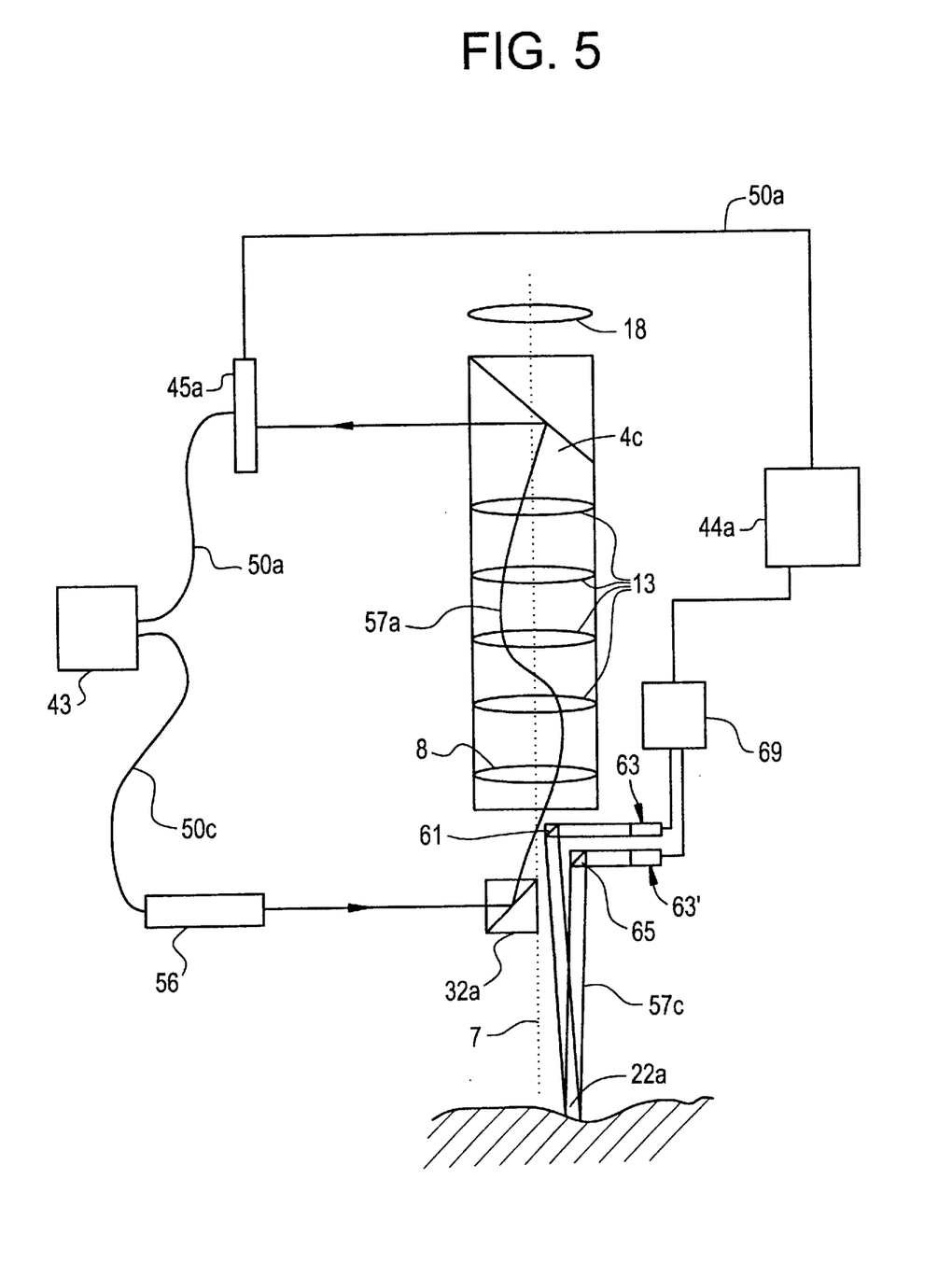
FIG. 5 shows a position system with distance measurement and magnification measurement.

FIG. 5 shows a laser 56 which is deflected into the microscope optical system 8, 13 via an adjustable beam splitter 32a. From the microscope optical system 8, 13, the beam 57a passes via a beam splitter 4c onto a measuring array 45a. The beam 57a can be observed through an eyepiece 18. The beam positions on the measuring array 45a and the corresponding positions of the inserting element 32a are used to determine the magnification or the position of the focal plane. The laser 56 is controlled via an interval switch 43 in order to minimize possible disturbances emanating from the measuring beam. The evaluation of the positional data is performed in a microprocessor 44a. The components described above are interconnected by connecting lines 50a and 50c.

The distance measurement is performed via a distance measuring system 69 from which light guides lead to the tails 63 and 63'. Use is made of laser light whose beam 57c is fed between the object and the microscope toward the first deflecting element 61. The beam reflected at the feature 22a on the object is deflected by the second deflecting element 65 toward the light guide tail 63' connected to the sensor. The distance measuring system 69 is connected to the processor 44a, with the result that the latter can determine real positions on the image section under examination from the distance values and the magnification values.

Figure 6:
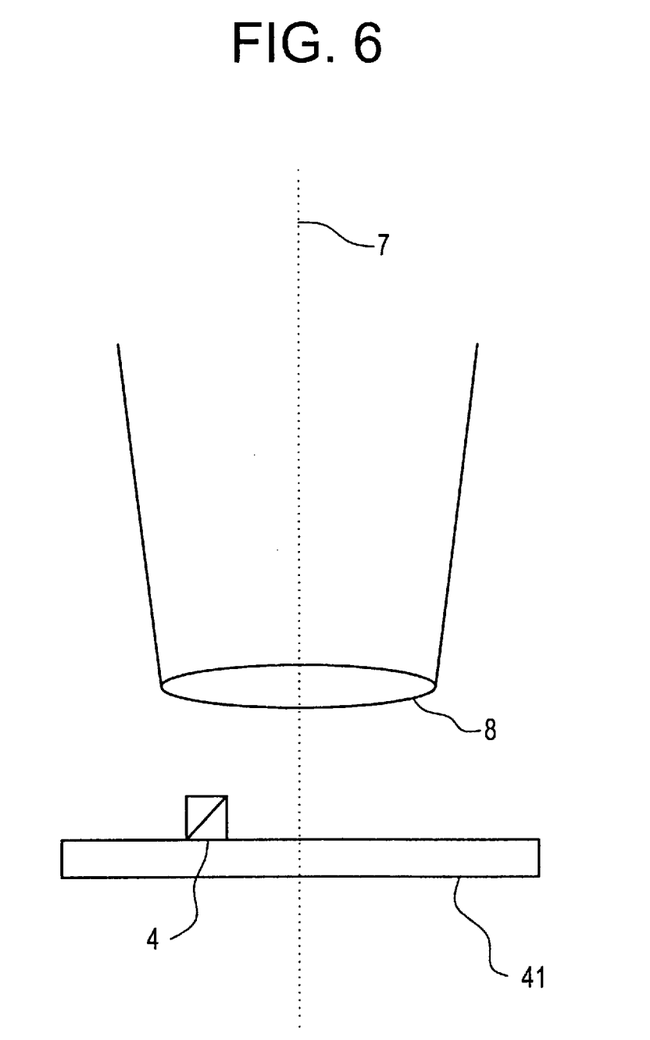
FIG. 6 shows a detail of a variant of the inserting and extracting elements of FIGS. 2–5.

FIG. 6 shows a thin glass plate, possibly with an antireflection coating, which carries one or more small inserting elements 4 which can be pushed in such a fashion as to be very near lenses, main objectives 8 etc. and cause only more partial—generally negligibly small—optical interference. The inserting elements represented in the remaining figures can be replaced by ones such as these. Reference is made once again expressly, in regard to this, to the PCT patent application WO-A-95 27 918, whose teaching regarding the inserting elements is deemed as disclosed herein.

Preference is given to a variant in combination with position detection in accordance with patent claims 20 to 26 of the abovementioned PCT patent application. The corresponding figures and the associated parts of the description of the figures are deemed as disclosed herein.

Further details and variants are described and characterized in the patent claims.

List of reference symbols

This list of reference symbols also contains reference symbols of figures which are contained in the abovementioned applications, since, as mentioned, these latter reference symbols or the features specified by these reference symbols and their corresponding parts of the description and drawings are deemed to have been co-disclosed for combination purposes as being within the scope of this invention. This applies, in particular, to microscopes with special beam paths and beam splitters and the devices for measuring the magnification and the distance from the microscope to the object.

1 First beam path; a, b
2 Second beam path (first beam paths positioned geometrically one above another); a, b
3 Mechanooptical switching element
3a–c Opaque and preferably silvered diaphragm
3d LCD shutter element
3e Micromechanical leaf-type mirror design
3f LCD exchangeable shutter element
4 Beam splitter
4a,b Beam splitter
4c Beam splitter for multi-beam extraction 4c1, 4c2
5 Sheet
5a Semicircular surface
5b Residual surface of the sheet 5
5c Circular segment surfaces
6 Axis for sheet
7 Central axis
7a,b Central axis
8 Main objective
8a Main objective
8b Main objective, exchangeable with 8a (different focal lengths)
8c Main objective
8d Main objective
9 Electronic image pick-up device
10 Display
10a Display
11 Mirror; a, b
12 Adjusting device; a–c
113 Zoom lens
14 Motor; a, b
15 Reciprocal drive
16 Lead
17 Light source
18 Eyepiece
19 Deflecting mirror
20 Push rod
21 Rigid mirror
22 object
22a feature on object
22A feature on object
23 Plane plate; a–d, a',b'
24 Pivot drive
25 Linkage
30 Leaf-type mirror of 3e
31 Tubular lens
32 Inserting element
32a Beam parts
32b Mirror
32c Second inserting element
33 Magnifying optical system
34 Arrows
35 Further mirror
36 Actuator
37 Beam
38 Deflecting mirror; a, b
39 Inverted prism
40 Balance weight
41 Backing plate; a–c; prismatic with integrated mirror
42 Color filter; a–f
43 Interval switch
44 Microprocessor
45 Measuring array; a
46 Reference array; a
47 Module for image data transmission
48 External image data input
49 Positioning motor for zoom lens 13; a, b
50 Connecting lines; a–g
51 Magnification display; a–c
52 Cam disk
53 Coupling
  53a between positioning motor 49b and zoom lens 13 or between 49 and 52
  53b between cam disk 32 and magnification display 51b
54 Mechanical tap
55 Pointer; a, b
56 Laser
57 Measuring beam; a–c,c1
58 Reference beam
59 Arrows for displaceability of the inserting element 32
60 Microscope beam path a–e
61 First deflecting element; a
62 Focusing element; a, b
63 Light guide tail; a, b
64 Light source; a
65 Second deflecting element
66 Sensor
67 Distance range; a
68 Connecting. line
69 Distance measuring system 70 Connection
71 Magnification measuring unit
72 Position determining system; a, b
73 Interferometer
74 Semireflective mirror
75 Reflector
76 Detector
77 Electromechanical adjusting element
78 Interferometer controller
79 Grating
80 Detector CCD
81 Stages
82 Microscope
83 Arrangement for measuring the magnification of the microscope
84 Arrangement for measuring the object/microscope separation
85 Position measuring system for determining the absolute position of the microscope in space in order also to be able to infer the position of the visual field on the object in accordance with knowledge of the object/microscope separation.
86 Tool box for various user programs
87 Command control device (computer mouse)
88 Demand control device for controlling the movement of the microscope (for example foot switch)
89 Data conditioning unit
90 Computer (workstation)
91 Control switch for microscope
92 Electromechanical control unit for microscope (zoom lens, focus etc.)
93 Light-emitting diodes; a–c
94 Optical fibers; a–c
95 Ends of the optical fibers; a–c
96 IR receptors; a–c
97 Microscope stand
98 Feedback
99 Leads; a–c
100 Reflectors with special surface
b Spacing of the measuring beams 57a and 57b
b' Spacing of the measuring beams 57a and 57b on the measuring array
d1,2 Stereobase
X Light source or tail of an interposed light guide
Xa Optical feeding system
Y Detector or tail of a light guide
Ya Outcoupling optical system

We claim:

1. A method for determining the distance of a feature (22a) on an object from a microscope in the direction of a central axis (7) of the microscope, in which at least one measurement signal is compared with a reference signal, the measurement signal comprising a light bundle along a light path (57c) from a light source (64) assigned to the microscope to the feature (22a) on the object, the bundle being directed from the light source (64) onto the feature (22a) on the object in order to be reflected or scattered there, the reflected or scattered light bundle being fed at least partly to a receiving unit having at least one sensor (66), wherein:

the light path (57c) is positioned in the vicinity of the central axis (7) of the microscope, and its axis is positioned at least approximately parallel thereto, and the receiving unit is connected optically and/or electronically to the light source (64), light from the light bundle detected at the sensor (66) in the receiving unit being compared and/or combined with light emitted from the light source (64), whereupon transit-time differences between the light pulses or modulations superimposed on the light bundle, and/or instances of interference or interference phenomena which occur are used to determine at least one variable which is a function of the difference between the two signals and which is used to derive the distance between the microscope and the feature (22a) on the object.

2. A method according to claim 1, wherein the light bundle emitted from the source (64) is temporally modulated, and incident light is fed in the receiving unit to the sensor (66), in order to detect the modulation, whereupon the phase shift between the outgoing light pulses from the source (64) and the light pulses incoming at the sensor (66) is measured electronically and directly, in order to determine therefrom the corresponding distance.

3. A method according to claim 1, wherein modulation or coding of the light bundle is performed by modulation in the light source.

4. A method according to claim 1, wherein light modulation is performed at a frequency of at least 10 MHz.

5. A method according to claim 1, wherein the light bundle comprises at least one beam, which is directed onto a point on the object.

6. A method according to claim 1, wherein the light bundle comprises at least one beam which has a coherence length which suffices for generating interference patterns but is bounded above, and wherein the position of the feature on the object is determined by coherence matching of an interferometer, the light source being varied in order thereby to achieve an arbitrary change in the coherence length and thus in the desired sensitivity.

7. A method according to claim 1, wherein in order to magnify the measuring range at least one coarse adjustment step or coarse measurement step is additionally provided.

8. A method according to claim 1, wherein for a modulated light signal the determination of a phase for position determination is carried out, and for a light signal which can be the same interference matching is also carried out to determine position, and the two determinations of position are used together to determine the relative position.

9. A method according to claim 1, wherein in addition to determination of distance between the microscope and feature (22a) on the object, determinations of position are also provided for the object (22) observed, which come from data on the focal plane and the magnification of the microscope, and also from positional data of the microscope, measurement of optical deflection by at least one light beam leading through the microscope optical system being provided for the purpose of determining magnification data.

10. A device for determining the distance of a feature (22a) on an object from a microscope in the direction of a central axis (7) of the microscope, comprising:

at least one device for generating a measurement signal and a reference signal, a receiving unit having at least one sensor (66) and at least one device for comparing the two signals, at least the measurement signal comprising a light bundle along a light path (57c) from a light source (64), assigned to the microscope, to the feature (22a) on the object, which bundle can be directed from the light source (64) onto the feature (22a) on the object, in order to be reflected or scattered there, at least a portion of the reflected or scattered light bundle being assigned to the receiving unit, wherein the light path (57c) is arranged in the vicinity of the central axis (7) of the microscope, and its axis is arranged at least approximately parallel thereto, and the receiving unit is connected optically and/or electronically to the device for generating the measurement signal, in the operating state the light from the light bundle detected at the sensor (66) in the receiving unit being compared and/or combined with the light emitted from the light source (64), and an analyzing unit, wherein transit-time differences between the light pulses or modulations superimposed on the light bundle, and/or instances of interference or interference phenomena which occur are used to determine at least one variable which is a function of the difference between the two signals and which is used to determine the distance between the microscope and the feature (22a) on the object.

11. A device according to claim 10, wherein in the sensor (66) is designed as a phase-determining sensor and renders determinable at least one variable, which is a function of the phase shift between light emitted from the light source (64) and incoming at the sensor.

12. A device according to claim 10 wherein a) the light source (64) or a light guide tail (63a) connected to the light source (64), is arranged transverse to the central axis (7) of the microscope and in the operating case emits a light bundle (57c) essentially toward the central axis (7), b) at least one first reflecting element (61), is provided such that at least a portion of the light bundle (57c) is deflected essentially parallel to the central axis (7) toward the object (22), and c) at least one second deflecting element (65) is provided such that at least a portion of the reflected or scattered light bundle (57c1) is deflected transverse to the central axis (7) toward the sensor (66) or toward a light guide tail (63b) connected to the sensor (66).

13. A device according to claim 12, wherein the first and/or the second deflecting element (61, 65) is arranged between the object (22) and the microscope optical system (8, 13).

14. A device according to claim 10, wherein the light source (64) comprises a modulation element which generates an oscillation with a frequency of at least 10 MHz.

15. A device according to claim 10, wherein the sensor is designed as a two-beam interferometer (73) through which the path length of a laser beam (57c) reflected at the object (22) can be determined by means of interference matching.

16. A method according to claim 1, wherein said microscope is a surgical microscope.

17. A device according to claim 10, wherein said microscope is a surgical microscope.

* * * * *